US010458701B2

(12) United States Patent
Destour et al.

(10) Patent No.: US 10,458,701 B2
(45) Date of Patent: Oct. 29, 2019

(54) METHOD FOR FRACTIONATING A STREAM OF CRACKED GAS, USING AN INTERMEDIATE RECIRCULATION CURRENT, AND RELATED PLANT

(71) Applicant: TECHNIP FRANCE, Courbevoie (FR)

(72) Inventors: Bruno Destour, Rueil Malmaison (FR); Yvon Simon, Andresey (FR); Aurélia Dadou, Puteaux (FR); David Chazallet, Courbevoie (FR)

(73) Assignee: TECHNIP FRANCE, Courbevoie (FR)

( * ) Notice: Subject to any disclaimer, the term of this patent is extended or adjusted under 35 U.S.C. 154(b) by 592 days.

(21) Appl. No.: 15/030,913

(22) PCT Filed: Oct. 23, 2014

(86) PCT No.: PCT/EP2014/072767
§ 371 (c)(1),
(2) Date: Apr. 21, 2016

(87) PCT Pub. No.: WO2015/059233
PCT Pub. Date: Apr. 30, 2015

(65) Prior Publication Data
US 2016/0258676 A1 Sep. 8, 2016

(30) Foreign Application Priority Data
Oct. 23, 2013 (FR) .................... 13 60349

(51) Int. Cl.
*F25J 3/02* (2006.01)
*C10L 3/00* (2006.01)
(Continued)

(52) U.S. Cl.
CPC ............ *F25J 3/0219* (2013.01); *C07C 5/327* (2013.01); *C07C 7/005* (2013.01); *C07C 7/09* (2013.01);
(Continued)

(58) Field of Classification Search
CPC .................. F25J 3/0219; F25J 2205/02–04
See application file for complete search history.

(56) References Cited

U.S. PATENT DOCUMENTS 4,496,381 A * 1/1985 Norenburg ............... C07C 7/04
62/630
5,421,167 A * 6/1995 Verma .................. C10G 70/043
62/631

(Continued)

FOREIGN PATENT DOCUMENTS

FR           2817767           6/2002
WO    WO 2011/004123 A2      1/2011
(Continued)

OTHER PUBLICATIONS

Search Report dated Jun. 12, 2014 (in French).
(Continued)

*Primary Examiner* — Tareq Alosh
(74) *Attorney, Agent, or Firm* — Locke Lord LLP; Alan B. Clement; Peter J. Fallon

(57) ABSTRACT

This method comprises:
forming an expanded intermediate recirculation stream (170) from a liquid (112, 128) obtained during an upstream cooling and/or intermediate cooling step, upstream from the downstream cooling step;
circulating the intermediate recirculation stream (170) at least in an upstream heat exchanger (42) to cool an upstream stream of cracked gas (102);
reintroducing the reheated intermediate recirculation stream (170) in a raw cracked gas (20) upstream from at least one compressor (36, 38) of a cooling and compression stage (24).

Figure 1:
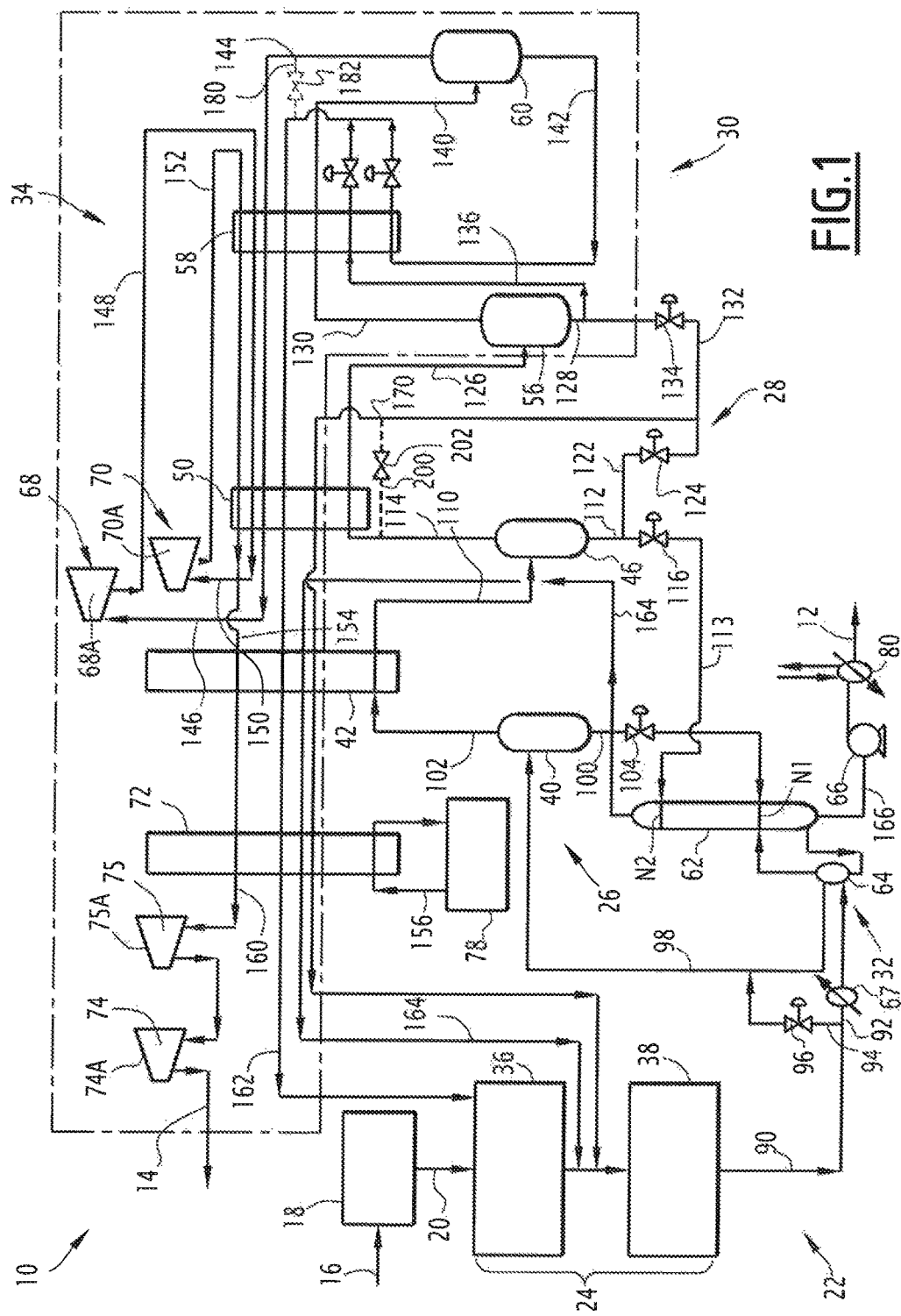

The upstream, intermediate and downstream cooling steps is carried out without a heat exchanger respectively of an upstream stream of cracked gas (102), an intermediate stream of cracked gas (114) and a downstream stream of cracked gas (140) with an external refrigeration cycle.

21 Claims, 2 Drawing Sheets

(51) Int. Cl.
*C10G 70/04* (2006.01)
*C07C 7/09* (2006.01)
*C07C 7/00* (2006.01)
*C10G 5/06* (2006.01)
*C10G 9/00* (2006.01)
*C07C 5/327* (2006.01)

(52) U.S. Cl.
CPC ............... *C10G 5/06* (2013.01); *C10G 9/002* (2013.01); *C10G 70/041* (2013.01); *C10G 70/043* (2013.01); *C10L 3/00* (2013.01); *F25J 3/0233* (2013.01); *F25J 3/0238* (2013.01); *F25J 3/0252* (2013.01); *F25J 3/0271* (2013.01); *C10G 2400/20* (2013.01); *C10G 2400/26* (2013.01); *C10L 2290/06* (2013.01); *C10L 2290/10* (2013.01); *C10L 2290/46* (2013.01); *C10L 2290/543* (2013.01); *F25J 2200/70* (2013.01); *F25J 2205/04* (2013.01); *F25J 2210/04* (2013.01); *F25J 2210/06* (2013.01); *F25J 2210/12* (2013.01); *F25J 2215/62* (2013.01); *F25J 2230/30* (2013.01); *F25J 2245/02* (2013.01); *F25J 2270/02* (2013.01); *F25J 2270/06* (2013.01); *F25J 2270/12* (2013.01); *F25J 2270/60* (2013.01); *Y02P 30/48* (2015.11)

(56) References Cited

U.S. PATENT DOCUMENTS

| | | | |
|---|---|---|---|
| 5,983,664 | A | 11/1999 | Campbell et al. |
| 6,271,433 | B1 | 8/2001 | Keady et al. |
| 6,526,777 | B1 | 3/2003 | Campbell et al. |
| 2002/0007101 | A1 | 1/2002 | Senetar et al. |
| 2004/0177646 | A1 | 9/2004 | Wilkinson et al. |
| 2006/0004242 | A1 | 1/2006 | Verma et al. |
| 2007/0199865 | A1 | 8/2007 | Pham Duc |
| 2008/0081938 | A1 | 4/2008 | Schultz et al. |
| 2009/0194461 | A1 | 8/2009 | Bras et al. |
| 2009/0282865 | A1 | 11/2009 | Martinez et al. |
| 2010/0043488 | A1 | 2/2010 | Mak et al. |
| 2010/0107685 | A1* | 5/2010 | Dragomir ............... C01B 3/506 62/617 |
| 2010/0263407 | A1 | 10/2010 | Paradowski et al. |
| 2011/0005273 | A1 | 1/2011 | Gahier et al. |
| 2012/0172649 | A1 | 7/2012 | Yadav et al. |
| 2012/0266630 | A1* | 10/2012 | Laugier ................... F16D 21/00 62/613 |

FOREIGN PATENT DOCUMENTS

| | | | | |
|---|---|---|---|---|
| WO | WO 2011/051614 A2 | 5/2011 | | |
| WO | WO 2011/051614 A3 | 5/2011 | | |
| WO | WO 2011/056712 A2 | 5/2011 | | |
| WO | WO 2011051614 A2 * | 5/2011 | ............. | C10G 70/04 |
| WO | WO 2012/089709 A2 | 7/2012 | | |
| WO | WO 2012/089709 A3 | 7/2012 | | |

OTHER PUBLICATIONS

PCT International Search Report dated Oct. 24, 2012 (Form PCT/ISA/220) and PCT Opinion (Form PCT/ISA/237) (in French) corresponding to International Application No. PCT/EP2011/074051 filed Dec. 26, 2011 (in French).

Joe T. Lynch et al., "Texas plant retrofit improves throughput, C2 recovery," Oil & Gas Journal (Jun. 3, 1996), pp. 41-48.

Search Report dated Mar. 12, 2014 corresponding to French Application No. 13 56061.

PCT Notification of Transmittal of the International Search Report and the Written Opinion of the International Searching Authority, or the Declaration dated Apr. 8, 2016 for International Application No. PCT/EP2015/081371 filed Dec. 29, 2015.

EP Search Report dated Jul. 20, 2015—EP Application No. 14307211.4-1361.

* cited by examiner

METHOD FOR FRACTIONATING A STREAM OF CRACKED GAS, USING AN INTERMEDIATE RECIRCULATION CURRENT, AND RELATED PLANT

This application is a National Stage application of international Patent Application Number, PCT/EP2014/072767, filed on Oct. 23, 2014, which claims priority to FR 13 60349, filed Oct. 23, 2013, the entire contents of which are incorporated herein by reference.

The present invention relates to a method for fractionating a stream of cracked gas from a hydrocarbon pyrolysis plant to obtain an ethylene-rich cut and a $C_2^+$ hydrocarbon-lean fuel stream, the method comprising the following steps:
  compression of the stream of raw cracked gas in at least one compressor of a cooling and compression stage to form a compressed cracked gas stream;
  upstream cooling and partial condensation, in at least one upstream heat exchanger, of an upstream stream of cracked gas, obtained from the compressed cracked gas stream, and separation of an upstream liquid in at least one upstream balloon to form an intermediate stream of cracked gas pre-cooled at first temperature;
  intermediate cooling and partial condensation of the intermediate stream of cracked gas in an intermediate heat exchanger and separation of an intermediate liquid in an intermediate separating balloon to form a downstream stream of cracked gas cooled to a second temperature lower than the first temperature;
  downstream cooling and partial condensation of the downstream stream of cracked gas in at least one downstream heat exchanger to a third temperature lower than the second temperature;
  introduction of the downstream stream of partially condensed cracked gas from the downstream heat exchanger in a downstream separator;
  recovery, at the head of the downstream separator, of a gas stream of high-pressure fuel, lean in $C_2^+$ hydrocarbons, and recovery, at the bottom of the downstream separator, of a downstream liquid, rich in $C_2^+$ hydrocarbons;
  passage of the stream of high-pressure fuel through the downstream exchanger and the intermediate exchanger to form a heated high-pressure fuel stream;
  expansion of the heated high-pressure fuel stream in at least one first dynamic expansion device to obtain a stream of partially expanded fuel;
  heating of the stream of partially expanded fuel through the downstream exchanger and the intermediate exchanger;
  treatment of at least one liquid stream obtained during the upstream cooling, intermediate cooling and downstream cooling steps to form the ethylene-rich cut.

The cracked gas comes from a hydrocarbon pyrolysis plant, such as a steam cracking furnace. The gas introduced in the pyrolysis plant advantageously has between 60% and 70% ethane, in association with propane, butane, naphtha, and/or diesel fuel.

The method of the aforementioned type is intended to treat cracked gas to obtain an ethylene cut having an ethylene content greater than 99.95 mol %, recovering more than 99.5 mol % of the ethylene contained in the cracked gas.

A method of the aforementioned type that makes it possible to obtain such performance levels is for example described in EP 1,215,459.

This method is intended to be carried out to treat very large volumes of cracked gas, for example greater than 50 tons, in particular greater than 100 tons per hour.

In order to guarantee both very high purity of the produced ethylene stream and a maximum ethylene recovery rate, it is necessary to cool the treated gas to temperatures below −100° C., and in particular below −120° C.

To that end, the stream of cracked gas is placed in a heat exchange relationship with ethylene circulating in an outside refrigeration cycle.

The ethylene refrigeration cycle generally comprises three thermal levels, with a first heat exchanger at approximately −50°, a second heat exchanger at approximately −75° and a third heat exchanger at approximately −100°.

After each heat exchange, the partially condensed cracked gas is introduced into a separator to discharge the formed liquid.

The collected liquids, which are generally rich in $C_2^+$ hydrocarbons, are sent to a treatment unit including at least one fractionating column. The fractionating column produces the stream containing the recovered ethylene using the cryogenic method.

The use of an external ethylene-based cooling cycle, with three thermal levels, significantly increases the energy consumption of the method. The investment necessary for the installation of the cycle is also significant.

To offset this problem. WO 2011/051614 describes a method in which the third cold level of the ethylene-based refrigeration cycle is eliminated and replaced by a double expansion of the stream of fuel in two successive dynamic expansion devices to provide the frigories necessary for low-temperature cooling of the stream of cracked gas.

This method therefore eliminates one thermal level from the ethylene refrigeration cycle, which limits the investment necessary for its implementation. It nevertheless retains its full effectiveness in terms of ethylene recovery rate, while having improved energy performance levels.

In some cases, it is desirable to still further reduce the required investment. This is for example the case for small ethylene production units, in which the installation and commissioning of an ethylene cycle is particularly costly, since it may represent up to 5% of the price of the equipment of the unit.

Furthermore, the initial supply of ethylene to start the unit, and its manipulation during commissioning of the refrigeration cycle, may prove complicated, in particular when it is difficult to convey ethylene to the unit.

One aim of the invention is therefore to obtain a cracked gas fractionating method that requires an even lower investment in particular to adapt to small units, while offering a very high ethylene recovery rate and satisfactory energy performance levels.

To that end, the invention relates to a method of the aforementioned type, characterized in that the method includes the following steps:
  forming an expanded intermediate recirculation stream from a liquid obtained during the upstream cooling and/or intermediate cooling steps, upstream from the downstream cooling step;
  circulating the intermediate recirculation stream at least in the upstream heat exchanger to cool the upstream stream of cracked gas;
  reintroducing the reheated intermediate recirculation stream in the raw cracked gas upstream from at least one compressor of the cooling and compression stage, the upstream, intermediate and downstream cooling steps being carried out without heat exchange respectively of the upstream stream of cracked gas, the intermediate stream of cracked gas and the downstream stream of cracked gas with an external refrigeration cycle, such as an ethylene cycle.

The method according to the invention may comprise one or more of the following features, considered alone or according to any technically possible combination(s):

- the pressure of the expanded intermediate recirculation stream is greater than 15%, and is advantageously comprised between 20% and 50% of the pressure of the compressed cracked gas stream;
- the pressure of the expanded intermediate recirculation stream is greater than 5 bars and is in particular comprised between 5 bars and 20 bars;
- the molar flow rate of the expanded intermediate recirculation stream is greater than 25% and is in particular comprised between 30% and 60% of the molar flow rate of the stream of raw cracked gas;
- the molar ethylene content in the expanded intermediate recirculation stream is greater than 50%, and is in particular comprised between 55% and 65%;
- the molar ethane content in the intermediate recirculation stream is comprised between 15% and 30%, the molar methane content in the intermediate recirculation stream being comprised between 10% and 20%;
- the ratio of the molar ethylene content to the molar hydrogen content in the compressed raw cracked gas stream, after reintroduction of the expanded intermediate recirculation stream, is greater than 1.3 times the ratio of the molar ethylene content to the molar hydrogen content in the raw cracked gas stream, before the reintroduction of the expanded intermediate recirculation stream in the raw cracked gas stream;
- the temperature of the intermediate recirculation stream is comprised between −75° C. and −95° C., after expansion, and before introduction in a heat exchanger;
- it comprises the formation of an expanded recirculation stream from at least one fraction of an intermediate liquid and/or at least one fraction of the downstream liquid, the expanded recirculation stream being introduced into the downstream heat exchanger, and/or into the intermediate heat exchanger, before being mixed with the raw cracked gas stream before the passage of the raw cracked gas stream in at least one compressor of the cooling and compression stage, the pressure of the expanded recirculation stream being lower than the pressure of the expanded intermediate recirculation stream;
- it comprises the injection of at least one fraction taken from the high-pressure fuel gas stream into the expanded recirculation stream;
- it comprises the withdrawal of a bypass stream from the intermediate cracked gas stream, upstream from the intermediate heat exchanger and the injection of the bypass stream, after expansion, in the expanded intermediate recirculation stream;
- it comprises forming at least one intermediate recirculation stream from the upstream liquid coming from the upstream separator balloon and the formation of at least one intermediate recirculation stream from the intermediate liquid from the intermediate separator balloon;
- it comprises providing a heat exchange relationship between at least one fraction of the compressed cracked gas stream and a refrigerant circulating in an outside refrigeration cycle, then its introduction into an upstream separator balloon to form the upstream stream of cracked gas.

the method comprising the following steps:

- passage of the partially expanded fuel stream coming from the intermediate exchanger in a second dynamic expansion device to form an expanded fuel stream;
- heating the expanded fuel stream from the second dynamic expansion device in the downstream heat exchanger and in the intermediate heat exchanger and in the upstream heat exchanger;
- compressing the stream of heated expanded fuel in at least one compressor coupled to at least one expansion turbine of the first dynamic expansion device and/or the second dynamic expansion device to form the $C_2^+$ hydrocarbon-lean fuel stream;
- the thermal power necessary for cooling of the upstream stream of cracked gas toward the first temperature is provided in the upstream heat exchanger by heat exchange with the intermediate recirculation stream and advantageously by heat exchange with the expanded fuel stream, without heat exchange with an outside refrigerant circulating in a refrigeration cycle;
- the thermal power necessary for cooling of the intermediate stream of cracked gas toward the second temperature is provided in the intermediate heat exchanger by heat exchange with the high-pressure fuel stream, by heat exchange with the partially expanded fuel stream, by heat exchange with the intermediate recirculation stream, and advantageously by heat exchange with the expanded fuel stream, without heat exchange with an outside refrigerant circulating in a refrigeration cycle;
- the thermal power necessary for cooling of the downstream stream of cracked gas to the third temperature is provided in the downstream heat exchanger by heat exchange with the high-pressure fuel stream, by heat exchange with the partially expanded fuel stream, advantageously by heat exchange with the expanded fuel stream, and advantageously by heat exchange with the recirculation gas stream, without heat exchange with an outside refrigerant circulating in a refrigeration cycle;
- the entire heated high-pressure fuel stream coming from the intermediate exchanger is introduced into the first dynamic expansion device, the entire partially expanded heated fuel stream from the intermediate exchanger being introduced into the second dynamic expansion device;
- the treatment step comprises introducing at least one stream formed from the upstream liquid, the intermediate liquid and/or the downstream liquid in a fractionating column and the production, in the fractionating column, of an ethylene-rich stream intended to form the ethylene-rich cut;
- the head stream from the fractionating column is conveyed in full toward the upstream heat exchanger and advantageously toward an upstream reheating exchanger, before being mixed with the raw cracked gas, without a fraction of the stream being condensed to be sent by reflux into the fractionating column;
- the molar hydrogen content level in the high-pressure fuel stream is greater than 75%;
- the first temperature is below −63° C., the second temperature is below −85° C., and the third temperature is below −125° C.;

the method includes a step for forming the stream of $C_2^+$ hydrocarbon-lean fuel from the stream of partially expanded fuel by compression in at least one compressor;

the method includes a step for expanding the stream of partially expanded fuel, reheating in at least one heat exchanger.

The invention also relates to a fractionating plant for a first stream of cracked gas coming from a hydrocarbon pyrolysis plant to obtain an ethylene-rich out and a $C_2^+$ hydrocarbon-lean fuel stream, the fractionating plant comprising:

a cooling and compression stage for the stream of raw cracked gas comprising at least one compressor, to form a stream of compressed cracked gas;

an upstream cooling and partial condensation assembly for an upstream stream of cracked gas, obtained from the stream of compressed cracked gas, the upstream assembly comprising at least one upstream heat exchanger, and at least one upstream separator balloon for an upstream liquid to form an intermediate stream of cracked gas pre-cooled to a first temperature;

an intermediate cooling and partial condensation assembly for the intermediate stream of cracked gas, the intermediate assembly comprising an intermediate heat exchanger and an intermediate separating balloon for an intermediate liquid to form a downstream stream of cracked gas cooled to a second temperature below the first temperature;

a downstream cooling and partial condensation assembly for the downstream stream of cracked gas to cool the downstream stream of cracked gas to a third temperature below the second temperature, the downstream assembly comprising at least one downstream heat exchanger;

a downstream assembly and an assembly for introducing the downstream stream of partially condensed cracked gas coming from the downstream heat exchanger into the downstream separator;

a recovery assembly, at the head of the downstream separator, for recovering a gaseous stream of high-pressure fuel, lean in $C_2^+$ hydrocarbons, and recovering, at the bottom of the downstream separator, a downstream liquid, rich in $C_2^+$ hydrocarbons;

a passage assembly for the stream of high-pressure fuel through the downstream exchanger and the intermediate exchanger to form a stream of reheated high-pressure fuel;

at least one dynamic expansion device for the stream of reheated high-pressure fuel to obtain a partially expanded fuel stream;

a passage assembly for the stream of partially expanded fuel through the downstream exchanger and the intermediate exchanger to reheat the stream of partially expanded fuel;

a treatment assembly for at least one liquid stream obtained in at least one of the upstream cooling, intermediate cooling, and downstream cooling assemblies to form the ethylene-rich cut;

characterized in that the plant comprises:

an assembly for forming an expanded intermediate recirculation stream from a liquid obtained in at least one of the upstream cooling and/or intermediate cooling assemblies, upstream from the downstream cooling assembly;

an assembly for circulating the intermediate recirculation stream at least in the upstream heat exchanger to cool the upstream stream of cracked gas;

an assembly for reintroducing the heated intermediate recirculation stream into the raw cracked gas upstream from at least one compressor of the cooling and compression stage, the upstream, intermediate and downstream cooling assemblies being configured to respectively cool the upstream stream of cracked gas, the intermediate stream of cracked gas and the downstream stream of cracked gas without heat exchange with an outside refrigeration cycle, such as an ethylene cycle.

Figure 2:
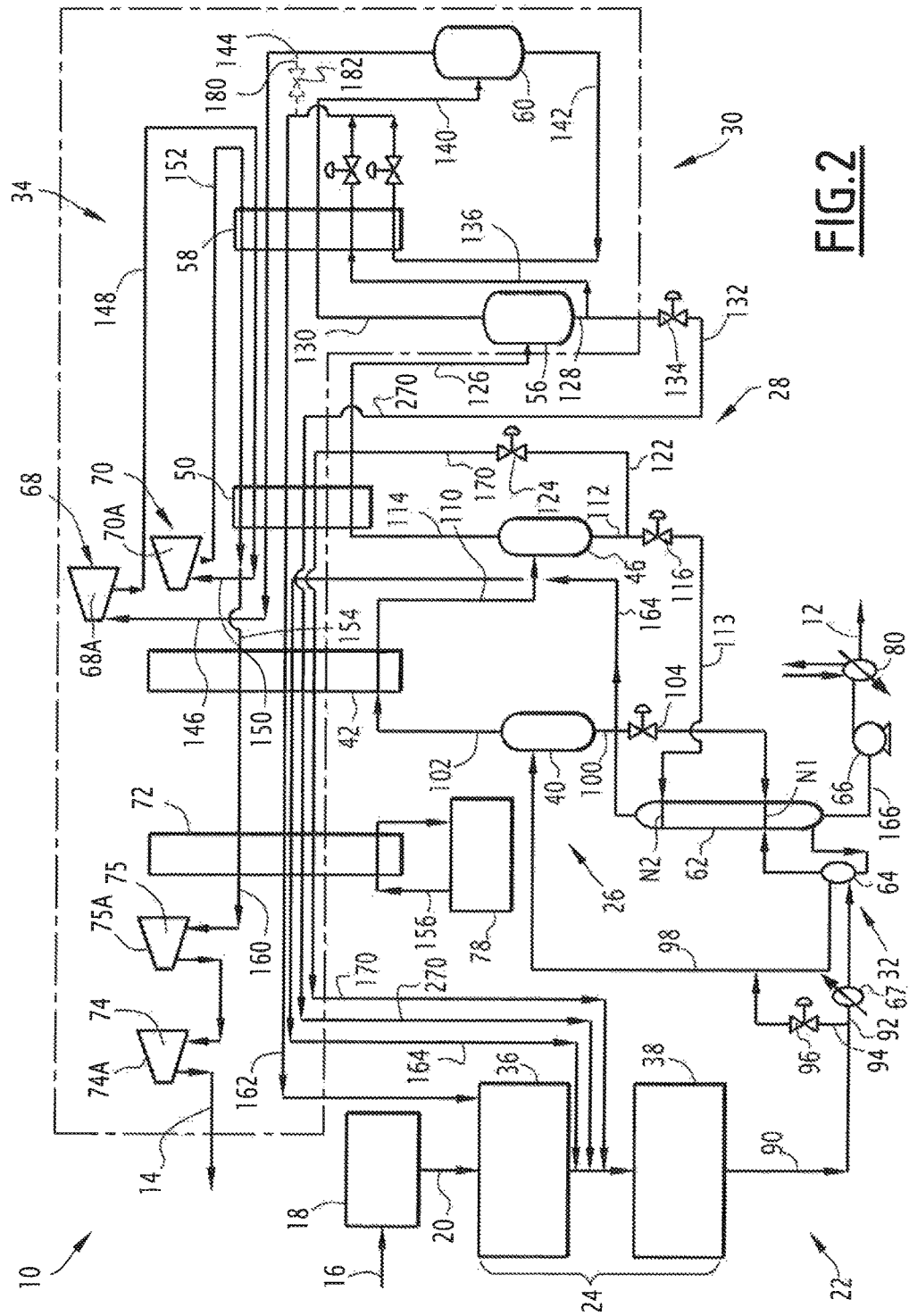

The invention will be better understood upon reading the following description, provided solely as an example and done in reference to the appended drawings, in which:

FIG. 1 is a functional block diagram of a first fractionating plant according to the invention, intended for the implementation of a first method according to the invention, and FIG. 2 is a detail of an alternative fractionating plant according to the invention.

Hereinafter, a same reference designates a stream circulating in a pipe and the pipe that transports that stream. Furthermore, unless otherwise indicated, the percentages are molar percentages and the pressures are to be understood in relative bars.

A first steam cracking unit 10 according to the invention is shown in FIG. 1.

This unit 10 is intended to form an ethylene-rich out 12 and a fuel gas stream 14 lean in $C_2^+$ hydrocarbons, from a load 16.

The unit 10 comprises a hydrocarbon pyrolysis plant 18 including a steam cracking furnace intended to produce a raw cracked gas stream 20. It further includes a fractionating plant 22 for the raw treated gas to form the stream of fuel gas 14 and the ethylene-rich cut 12.

The load 16 is advantageously formed by at least 60 mol % of ethane, in association with propane, butane, naphtha and/or diesel fuel.

The steam cracking furnace 18 is able to circulate the load 16 to heat it to a temperature above 800° C. This causes the thermal cracking of the hydrocarbon molecules contained in the load 16 in order to form the stream of raw cracked gas 20.

The fractionating plant 22 successively includes a cooling and compression stage 24, and an upstream assembly 26, an intermediate assembly 28 and a downstream assembly 30 for cooling and separating the cracked gas.

According to the invention, the upstream assembly 26, the intermediate assembly 28 and the downstream assembly 30 have no outside cooling cycle, in particular using ethylene.

The plant 22 further includes a treatment assembly 32 for liquids formed in the assemblies 26 to 30, and the expansion and heating assembly 34 for the fuel gas.

The compression and cooling stage 24 includes a cooling device (not shown), a primary compressor 36 and a secondary compressor 38, the secondary compressor 38 being positioned downstream from the primary compressor 36.

The upstream cooling and separating assembly 26 includes a first upstream separator balloon 40, an upstream heat exchanger 42, and a second upstream separator balloon 46.

The intermediate cooling and separating assembly 28 includes, from upstream to downstream, an intermediate heat exchanger 50 and an intermediate separator balloon 56. In this example, the intermediate assembly 28 comprises a single intermediate heat exchanger 50.

The downstream cooling and separating assembly 30 comprises a downstream heat exchanger 58, and a downstream separator balloon 60 intended to produce the stream of fuel gas.

The liquid treatment assembly 32 includes a fractionating column 62, a reboiling heat exchanger 64, and a column bottom pump 66.

In this example, the assembly 32 further advantageously comprises a backup heat exchanger 67, able to provide variable cooling thermal power based on the thermal cooling power provided by the reboiling heat exchanger 64. This backup heat exchanger 67 is for example supplied with refrigerant by propylene.

The expansion and heating assembly 34 comprises a first dynamic expansion device 68, and advantageously a second dynamic expansion device 70. The devices 68, 70 each have at least one dynamic expansion turbine 68A, 70A.

The expansion and heating assembly 34 further includes a reheating heat exchanger 72, a first compression device 74 and a second compression device 75, the devices 74 and 75 each having at least one compressor 74A and 75A, which are each coupled to a respective expansion turbine 68A, 70A of the first dynamic expansion device 68 and the second dynamic expansion device 70.

The reheating heat exchanger 72 cools a refrigerant circulating in a propylene refrigeration cycle 78. The propylene cycle 78 includes a bottom heat exchanger 80 placed downstream from the column bottom pump 66. The exchanger 80 can be integrated into the exchanger 72.

A first method according to the invention, implemented in the unit 10 for treating the stream of cracked gas resulting from the steam cracking of the load 16, will now be described.

Initially, the load 16 containing a majority of ethane is introduced into the steam cracking furnace 18 to be heated to a temperature greater than 800° C. and undergo thermal cracking.

A stream of raw cracked gas 20 is extracted from the furnace 18 at a temperature above 800° C. and at a pressure greater than 1 bar.

This stream 20 is next cooled and introduced into the primary compressor 36 to be compressed at a pressure greater than 10 bars substantially lower than the pressure in the fractionating column 62, then in the secondary compressor 38 to be compressed at pressure greater than 30 bars.

The compressed stream of cracked gas 90 coming from the secondary compressor 38 is next separated into a first reboiling fraction 92 and a second fraction 94.

In the example shown in FIG. 1, the reboiling fraction 92 is first inserted into the backup heat exchanger 67 to be partially cooled therein, by a thermal power commanded as a function of the thermal power needed by the reboiling heat exchanger 64.

The reboiling fraction 92 is introduced into the reboiling heat exchanger 64 to be cooled and partially condensed therein.

The second fraction 94 is passed through a first flow rate control valve 96, before being mixed with the reboiling fraction 92 coming from the exchanger 64 to form a partially condensed compressed cracked gas stream 98.

In one alternative of the method, the cracked gas stream 90 can advantageously circulate, partially or completely, through the reheating heat exchanger 72 and/or the backup heat exchanger 67, before the separation into the fractions 92 and 94, in order to cool in the exchanger 72 and/or in the backup heat exchanger 67.

The molar ratio of the first reboiling fraction 92 to the second fraction 94 is comprised between 0% and 20%. The stream of partially condensed cracked gas 98 contains at least 15 mol % of liquid. It has a temperature below −30° C.

Then, the stream 98 is introduced into the first upstream separator balloon 40 to form a first upstream liquid 100 and an upstream stream of cracked gas 102.

The first upstream liquid 100 is taken from the bottom of the first separator balloon 40 and is introduced at a lower level N1 of the fractionating column 62, after passage and expansion in a second flow rate control valve 104.

The pressure in the fractionating column 62 is advantageously comprised between 10 bars and 14 bars.

The upstream stream of cracked gas 102 is next introduced into the upstream heat exchanger 42. It is cooled and partially condensed in the upstream heat exchanger 42.

According to the invention, and as will be seen below, the cooling and partial condensation of the upstream stream of cracked gas 102 does not require the use of an outside refrigerant, circulating in a refrigeration cycle, in particular with ethylene.

The upstream stream of cracked gas 102 is cooled to a first temperature below −63° C. and in particular substantially comprised between −63° C. and −78° C. in the upstream heat exchanger 42.

At the outlet of the upstream heat exchanger 42, a partially condensed upstream stream 110 of cracked gas is obtained. This upstream stream of partially condensed cracked gas 110 is introduced into the second upstream separator balloon 46.

The molar liquid content level in the upstream stream of partially condensed cracked gas 110 is comprised between 30% and 60%.

In the second upstream separator balloon 46, the upstream stream of partially condensed cracked gas 110 separates into a second upstream liquid 112 and an intermediate gas stream 114 of cracked gas cooled to a first temperature below −63° C.

The second upstream liquid 112 is recovered at the bottom of the second upstream separator balloon 46. A first fraction 113 of the second upstream liquid 112 passes in a third flow rate control valve 116 and is introduced, after expansion, at a level N2 of the fractionating column 62 situated above the level N1, advantageously at the head of the column 62.

The intermediate stream of cracked gas 114 is introduced into the first intermediate heat exchanger 50 to be cooled therein to a temperature below −85° C. and to form a partially condensed intermediate stream 126 of cracked gas. The stream 126 has a temperature below −85° C., in particular comprised between −105° C. and −120° C., and a liquid content level comprised between 5 mol % and 30 mol %.

In the method according to the invention, the cooling of the stream 114 is done by simple passage in an intermediate heat exchanger 50, without having to pass in another intermediate heat exchanger, or without thermal contact with an outside refrigerant circulating in an outside refrigeration cycle, in particular an ethylene cycle.

The partially condensed intermediate stream of cracked gas 126 is next introduced into the intermediate separator balloon 56 to form an intermediate liquid 128 and downstream gas stream 130 of cracked gas.

According to the invention, at least one expanded intermediate recirculation stream 170 is formed from a liquid 112, 128 obtained during the upstream cooling and/or intermediate cooling steps, upstream from the downstream cooling step.

In this example, the expanded intermediate recirculation stream 170 is formed from a second fraction 122 of the upstream liquid 112 and from a first fraction 132 of the intermediate liquid 128.

To that end, the second fraction 122 of the upstream liquid 112 is introduced and expanded in a fourth control valve 124. The molar flow rate of the second fraction 122 of the upstream liquid 112 advantageously represents between 50 mol % and 90 mol % of the molar flow rate of the upstream liquid 112.

The first fraction 132 of the second intermediate liquid 128 is introduced and expanded in a fifth flow rate control valve 134.

A second recirculation fraction 136 of the second intermediate liquid 128 is sub-cooled in the downstream heat exchanger 58, as will be seen later.

The molar flow rate of the first fraction 132 of the intermediate liquid 128 advantageously represents between 70 mol % and 100 mol % of the molar flow rate of the intermediate liquid 128.

The fractions 122, 132 are next mixed to form the intermediate recirculation stream 170.

The temperature of the intermediate recirculation stream 170 is comprised between −75° C. and −95° C., after expansion in the valves 124, 134, and before introduction in the heat exchanger 50.

The intermediate recirculation stream 170 is next reheated through the intermediate heat exchanger 50, the upstream heat exchanger 42 and the reheating heat exchanger 72.

It is next reinjected into the raw cracked gas 20, at the compression and cooling stage 24, upstream from at least one compressor 36, 38.

In the example shown in FIG. 1, the intermediate recirculation stream 170 is reinjected into the raw cracked gas 20 between the first compressor 36 and the second compressor 38.

According to the invention, the intermediate recirculation stream 170 is not completely expanded. The stream 170 is in fact expanded at medium pressure, making it possible to reinject it after the first compressor 36.

Thus, the pressure of the expanded intermediate recirculation stream 170, after expansion in the valves 124, 134 and before its passage in the intermediate heat exchanger 50, is greater than 15% and is advantageously comprised between 20% and 50% of the pressure of the compressed cracked gas stream 90.

Advantageously, the pressure of the expanded intermediate recirculation stream 170 is greater than 5 bars, and is in particular comprised between 5 bars and 30 bars, in particular between 8 bars and 15 bars.

The molar flow rate of the intermediate recirculation stream 170 is high. This molar flow rate is 25% higher than the molar flow rate of the raw cracked gas stream 20 before passage in the cooling and compression stage 24. This molar flow rate is in particular comprised between 30% and 60% of the molar flow rate of the stream of raw cracked gas 20, advantageously between 40% and 60% of the molar flow rate of the stream of raw cracked gas 20.

The intermediate recirculate stream 170 is rich in ethylene. The molar content of ethylene in the intermediate recirculation stream 170 is advantageously greater than 50%, and is in particular comprised between 55% and 65%.

Typically, the molar content level of ethane in the intermediate recirculation stream 170 is comprised between 15% and 30%, the molar content level of methane in the intermediate recirculation stream 170 being comprised between 10% and 20%.

Advantageously, the intermediate recirculation stream 170 includes less than 3 mol % of hydrogen, and less than 1 mol % of compounds including three or more carbon molecules.

One major advantage of this invention is that the typical molar composition of the stream 170 is substantially constant over time, irrespective of the ethane content in the stream of raw cracked gas 20. This composition varies little with the conversion of the load 16 in the furnace 18. The fractionating method according to the invention is therefore stabilized by the addition of the stream 170 into the raw cracked gas stream 20, even if the composition of the raw cracked gas 20 varies.

The stream 170 enriches the stream of raw cracked gas 20 with ethylene, after its reinjection in the stream 20.

Thus, the ratio of the molar ethylene content to the molar hydrogen content in the compressed raw cracked gas stream 90, after reintroduction of the expanded intermediate recirculation stream 170, is greater than 1.3 times, in particular greater than 1.5 times, the ratio of the molar ethylene content to the molar hydrogen content in the raw cracked gas stream 20, before reinjection of the expanded intermediate recirculation stream 170.

This has the beneficial effect of increasing the partial ethylene pressure and condensing the ethylene in the streams 90, 98, 102, 114, 130 at a higher temperature, reducing the energy cost.

The downstream cracked gas stream 130 is introduced into the downstream heat exchanger 58 to be cooled therein and to form a downstream stream 140 of partially condensed cracked gas. The temperature of the stream 140, at the outlet of the downstream heat exchanger 58, is lower than −125° C., and is in particular comprised between −125° C. and −140° C.

The stream 140 is next introduced into the downstream separator balloon 60 to be separated therein into a downstream liquid 142 and a stream of fuel gas 144 at a high pressure intended to be expanded. The stream of fuel gas 144 includes more than 75 mol % of hydrogen and less than 0.5 mol % of $C_2^+$ hydrocarbons.

The stream 144 is introduced a first time into the downstream heat exchanger 58 to be reheated by countercurrent heat exchange with the downstream stream 130 of cooled cracked gas, then in the heat expander 50 to be reheated therein by heat exchange with the first intermediate stream of cracked gas 114 up to a temperature above −85° C.

The high-pressure fuel gas stream 146 reheated to a temperature above −85° C. is next introduced into a dynamic expansion turbine 68A of the first dynamic expansion device 68 to be expanded to a pressure below 12 bars and to form a stream 148 of fuel gas at an intermediate pressure.

The temperature of the stream 148 is below −150° C. The stream 148 is then introduced again into the downstream heat exchanger 58, then into the intermediate heat exchanger 50 to successively reheat by heat exchange with the stream 130 and the stream 114, respectively, as previously described.

This passage of the stream 148 through the exchangers 50, 58 is done between a turbine 68A of the first device 68 and a turbine 70A of the second device 70.

Advantageously, the stream 150 of fuel gas reheated at an intermediate pressure is next introduced into a dynamic expansion turbine 70A of the second dynamic expansion device 70 to be expanded therein at a pressure below 4 bars and to form a cooled stream of fuel gas 152 at a low pressure.

The temperature of the stream 152 is then below −115° C., and its pressure is below 4 bars.

The stream 152 is next successively introduced into the downstream heat expander 58, then into the heat exchanger 50 to be reheated therein countercurrent to the stream 130 and the stream 114, respectively, as described above.

The stream of reheated low-pressure fuel gas 154 coming from the first intermediate heat exchanger 50 is next successively introduced into the upstream heat exchanger 42 to be placed in a heat exchange relationship with the gaseous stream of cracked gas 102, then in the reheating heat exchanger 72.

In the reheating heat exchanger 72, the stream 154 reheats by heat exchange with the propylene refrigerant 156 circulating in the refrigeration cycle 78.

The stream 160 of low-pressure reheated fuel gas coming from the exchanger 72 thus has a pressure close to the atmospheric pressure.

The stream 160 is next successively introduced into the compressor 75A of the second compression device 75, then into the compressor 74A of the downstream compression device 74 to form the fuel stream 14 intended to supply the grid of the plant. The pressure of the stream 14 is greater than 5 bars.

The ethylene content in the high-pressure fuel gas 144, as in the fuel gas 14, is below 0.5 mol %. The ethylene recovery rate in the plant is above 99.5%.

The stream of fuel 14 advantageously comprises more than 99% of the methane contained in the stream of raw cracked gas 20.

The downstream liquid 142 includes more than 25 mol % of $C_2^+$ hydrocarbons. It is introduced into the downstream heat exchanger 58 to be sub-cooled therein to a temperature below −130° C.

After the passage in the exchanger 58, the liquids 136, 142 are expanded, then are mixed and successively introduced into heat exchangers 58, 50, 42 and 72 to reheat and evaporate by heat exchange with the respective streams circulating in these exchangers.

They then form a preheated recirculation gaseous stream 162 that has a temperature above 10° C. The gaseous stream 162 is reintroduced into the stream of raw cracked gas 20, in the primary compressor 36.

The recirculation gaseous stream 162 is expanded at a low pressure. It is thus expanded at a pressure lower than that of the intermediate recirculation stream 170, in particular 40% lower than the pressure of the intermediate recirculation stream 170.

The pressure of the recirculation gaseous stream 162, before passage in the downstream heat exchanger 58, is lower than 5 bars, in particular lower than 2 bars.

The fractionating column 62 produces a methane-rich head stream 164 and an ethylene-rich bottom stream 166.

The head stream 164 is introduced, after reheating in the upstream heat exchanger 42, then after reheating in the reheating heat exchanger 72, into the raw cracked gas stream 20, between the primary compressor 36 and the secondary compressor 38.

The bottom stream 166 coming from the fractionating column 62 is pumped by the pump 66, before being introduced into the recovery heat exchanger 80 (which can be incorporated in the exchanger 72). It is then reheated in contact with the propylene forming the refrigerant of the cycle 78. After passage in the exchanger 80, the ethylene-rich out 12 is formed. This cut 12 includes more than 99.5 mol % of the ethylene contained in the stream of raw cracked gas 20.

According to the invention, the upstream stream of cracked gas 102, which has been cooled to a temperature comprised between −30° C. and −50° C. owing to the refrigeration formed by the exchangers 64 and 67, is next cooled to a temperature below −63° C. in the exchanger 42, then to a temperature below −85° C. in the exchanger 50, and next to a temperature below −125° C. in the exchanger 58.

This cooling is done exclusively by heat exchange with the stream of high-pressure fuel gas 144, with the stream of partially expanded fuel gas 148, advantageously with the stream of expanded fuel gas 152, and by reheating the recirculation stream 162, associated with reheating of the intermediate recirculation stream 170.

It is therefore not necessary to provide an outside refrigeration cycle, in particular using ethylene. This decreases the energy consumption of the method and the investment necessary to carry it out.

The method according to the invention is therefore particularly suitable for small and medium capacity units for which the investment and upkeep costs must be minimized.

It is thus possible to have a low specific refrigeration power, while keeping an ethane recovery rate greater than 99.5% and producing an ethylene-rich cut 12.

This result is obtained by decreasing the investment necessary for the plant, since it is no longer necessary to provide equipment necessary for the implementation of an outside refrigeration cycle using ethylene, such as compressors, exchangers and separator balloons.

The method according to the invention can also be started without it being necessary to initially provide ethylene, for example in places that are difficult to access.

Examples of temperature, pressure, molar flow rate and composition of the flows 20, 90, 170 and 144 are given as an illustration in the table below.

|  | Flow | | | |
|---|---|---|---|---|
|  | 20 | 90 | 170 | 144 |
| Flow rate (base 100) | 100 | 170 | 50 | 2 |
| Temperature (° C.) | Ambient | Ambient at −20° C. | −75° C. to −95° C. | −130° C. to −155° C. |
| Pressure (bar) | 0.8 | 35 | 10.5 | 1 |
| Composition |  |  |  |  |
| Hydrogen | 36% | 22% | 2% | 15% |
| Methane | 7% | 12% | 15% | 53% |
| Ethylene | 34% | 44% | 60% | 29% |
| Ethane | 21% | 21% | 22% | 3% |
| C3+ | 2% | 1% | 0% | 0% |

This table illustrates the increase in the ethylene content in the flow 90 owing to the flow 170 as well as its stabilizing effect. The increase in this content level at a constant pressure creates the increase in the partial ethylene pressure, which makes it possible to condense the ethylene at a higher temperature and with a lower energy cost.

The power consumed by the compressors is given in the table below, in the case of an expansion at medium pressure of the intermediate recirculation stream 170: the power is expressed in base 100 relative to the compression stage 24 of the method according to WO 2011/051614.

| Power consumed (base 100) | Method according to WO 2011/051614 | Method according to the invention |
|---|---|---|
| Compression stage 24 | 100 | 120 |
| Refrigerant with propylene | 60 | 60 |
| Refrigerant with ethylene | 20 | — |
| Total | 180 | 180 |

The method according to the invention makes it possible to obtain a consumed thermal power similar to that of the advantageous method described in WO 2011/051614, but without requiring the implementation of an ethylene cycle.

This result is obtained particularly surprisingly with an expansion of the intermediate recirculation stream 170 at a medium pressure, and not a low pressure, as is generally done to obtain the coldest possible post-expansion temperatures.

In one alternative of the method, shown in dotted lines in FIG. 1, a fraction 180 of the head stream of fuel gas 144 is withdrawn and injected into the gaseous recirculation stream 162, after expansion in a control valve 182.

The ratio of the molar flow rate of the fraction 180 to the molar flow rate of the head stream of fuel gas 144 before withdrawal is less than 5%, and in particular comprised between 0.5% and 2%.

In another alternative of the method, shown in dotted lines in FIG. 1, a bypass stream 200 is withdrawn from the intermediate stream of cracked gas 114, upstream from the intermediate heat exchanger 50. The bypass stream 200 is expanded in the control valve 202, then is injected in the expanded intermediate recirculation stream 170.

The ratio of the molar flow rate of the bypass stream to the molar flow rate of the intermediate stream of cracked gas 114 before the withdrawal is less than 5%, and in particular comprised between 1% and 3%.

In another alternative of the method, the liquids 136 and 142 are introduced separately in the heat exchangers 50, 42, 72 to reheat, before being reintroduced into the stream of raw cracked gas 20.

In one alternative, each dynamic expansion device 68 comprises a plurality of dynamic expansion turbines, for example 2 to 3 dynamic expansion turbines. In another alternative, an additional compressor is placed downstream from the compressors 76A, 76B to compress the fuel gas 14 at a higher pressure.

In other alternatives, the treatment unit comprises a plurality of fractionating columns as for example described in EP 1,215,459.

The method partially illustrated in FIG. 2 differs from that illustrated in FIG. 1 in that it includes the formation of a first intermediate recirculation stream 170 from the second fraction 122 of the upstream liquid 112 and the formation of a second intermediate recirculation stream 270, different from the first intermediate recirculation stream 170, from the first fraction 132 of the intermediate liquid 128.

Each stream 170, 270 is next reheated separately through the intermediate heat exchanger 50, the upstream heat exchanger 42 and the reheating heat exchanger 72.

Each stream 170, 270 is next reinjected into the raw cracked gas 20, at the compression and cooling stage 24, upstream from at least one compressor 36, 38.

It will be noted, as shown in FIG. 1, that the entire stream of high-pressure fuel 144 is reheated successively in the downstream heat exchanger, and in the intermediate heat exchanger 50 before being introduced in full in the first dynamic expansion device 68.

Likewise, the entire stream of partially expanded fuel 148 coming from the first dynamic expansion device 68 is successively passed in the downstream exchanger 58 and in the intermediate exchanger 50, before being introduced in full in the second dynamic expansion device 70.

The entire expanded fuel stream 152 from the second dynamic expansion device 70 is next introduced into the downstream heat exchanger 58 and into the intermediate heat exchanger 50.

Thus, the recovery of frigories is maximal to allow cooling of the gas.

It will further be noted that the balloons 40, 46, 56 and 60 are simple separator balloons, and not distillation columns. Thus, these balloons have no plates or trim.

The fractionating column 62 is a column of the "stripper" type. Thus, the methane-rich head stream 164 coming from the column 62 is completely returned to the raw cracked gas 20, without a fraction of this stream 164 being condensed to be sent in reflux into the column 62.

The invention claimed is:

1. A method for fractionating a stream of cracked gas from a hydrocarbon pyrolysis plant to obtain an ethylene-rich cut and a C2+ hydrocarbon-lean fuel stream, the method comprising:
   compressing the stream of raw cracked gas in at least one compressor of a cooling and compression stage to form a compressed cracked gas stream;
   upstream cooling and partial condensing, in at least one an upstream heat exchanger, of an upstream stream of cracked gas, obtained from the compressed cracked gas stream, and separation of an upstream liquid in at least one upstream balloon to form an intermediate stream of cracked gas pre-cooled at a first temperature;
   intermediate cooling and partial condensing of the intermediate stream of cracked gas in an intermediate heat exchanger and separation of an intermediate liquid in an intermediate separating balloon to form a downstream stream of cracked gas cooled to a second temperature lower than the first temperature;
   downstream cooling and partial condensing of the downstream stream of cracked gas in at least one downstream heat exchanger to a third temperature lower than the second temperature;
   introducing the downstream stream of partially condensed cracked gas from the downstream heat exchanger in a downstream separator;
   recovering, at the head of the downstream separator a gas stream of high-pressure fuel, lean in C2+ hydrocarbons, and recovering, at the bottom of the downstream separator, a downstream liquid, rich in C2+ hydrocarbons;
   passing of the stream of high-pressure fuel through the downstream exchanger and the intermediate exchanger to form a heated high-pressure fuel stream;
   expanding the heated high-pressure fuel stream in at least one first dynamic expansion device to obtain a stream of partially expanded fuel;
   heating of the stream of partially expanded fuel through the downstream exchanger and the intermediate exchanger;
   treating at least one liquid stream obtained during the upstream cooling, intermediate cooling and downstream cooling to form the ethylene-rich cut;

forming an expanded intermediate recirculation stream from a liquid obtained during the upstream cooling and/or intermediate cooling, upstream from the downstream cooling;

circulating the expanded intermediate recirculation stream at least in the upstream heat exchanger to cool the upstream stream of cracked gas;

reintroducing the reheated intermediate recirculation stream in the raw cracked gas upstream from at least one compressor of the at least one compressor of the cooling and compression stage, the upstream, intermediate and downstream cooling being carried out without heat exchange respectively of the upstream stream of cracked gas, the intermediate stream of cracked gas and the downstream stream of cracked gas with an external refrigeration cycle, wherein passing the stream of high-pressure fuel through the downstream exchanger and the intermediate exchanger includes passing the stream of high-pressure fuel through the downstream exchanger and the intermediate exchanger without passing the stream of high-pressure fuel through the upstream heat exchanger between the head of the downstream separator and the at least one first dynamic expansion turbine.

2. The method according to claim 1, wherein the pressure of the expanded intermediate recirculation stream is greater than 15% of the pressure of the compressed cracked gas stream.

3. The method according to claim 1, wherein the pressure of the expanded intermediate recirculation stream is greater than 5 bars.

4. The method according to claim 1, wherein the molar flow rate of the expanded intermediate recirculation stream is greater than 25% of the molar flow rate of the stream of raw cracked gas.

5. The method according to claim 1, wherein the molar ethylene content in the expanded intermediate recirculation stream is greater than 50%.

6. The method according to claim 5, wherein the molar content level of ethane in the expanded intermediate recirculation stream is comprised between 15% and 30%, the molar content level of methane in the expanded intermediate recirculation stream being comprised between 10% and 20%.

7. The method according to claim 1, wherein the ratio of the molar ethylene content to the molar hydrogen content in the compressed raw cracked gas stream, after reintroduction of the expanded intermediate recirculation stream, is greater than 1.3 times the ratio of the molar ethylene content to the molar hydrogen content in the raw cracked gas stream, before the reintroduction of the expanded intermediate recirculation stream in the raw cracked gas stream.

8. The method according to claim 1, wherein the temperature of the intermediate recirculation stream is comprised between −75° C. and −95° C., after expansion, and before introduction in the upstream heat exchanger.

9. The method according to claim 1, comprising forming an expanded recirculation stream from at least one fraction of the intermediate liquid and/or at least one fraction of the downstream liquid, and introducing the expanded recirculation stream into the downstream heat exchanger, and/or into the intermediate heat exchanger, before mixing the expanded recirculation stream with the raw cracked gas stream before the passage of the raw cracked gas stream in at least one compressor of the at least one compressor of the cooling and compression stage, the pressure of the expanded recirculation stream being lower than the pressure of the expanded intermediate recirculation stream.

10. The method according to claim 9, comprising injection of at least one fraction taken from the high-pressure fuel gas stream into the expanded recirculation stream.

11. The method according to claim 1, comprising withdrawing a bypass stream from the intermediate cracked gas stream, upstream from the intermediate heat exchanger injecting the bypass stream, after expansion, in the expanded intermediate recirculation stream.

12. The method according to claim 1, comprising forming the at least one intermediate recirculation stream from the upstream liquid coming from the upstream separator balloon and forming at least one additional intermediate recirculation stream from the intermediate liquid-from the intermediate separator balloon.

13. The method according to claim 1, comprising providing a heat exchange relationship between at least one fraction of the compressed cracked gas stream and a refrigerant circulating in an outside refrigeration cycle, introducing said at least one fraction into the upstream separator balloon to form the upstream stream of cracked gas.

14. A fractionating plant for a first stream of cracked gas coming from a hydrocarbon pyrolysis plant to obtain an ethylene-rich cut and a C2+ hydrocarbon-lean fuel stream, the fractionating plant comprising:

a cooling and compression stage for the stream of raw cracked gas comprising at least one compressor, to form a stream of compressed cracked gas;

an upstream cooling and partial condensation stage for an upstream stream of cracked gas, obtained from the stream of compressed cracked gas, the upstream stage comprising an upstream heat exchanger, and at least one upstream separator balloon for an upstream liquid to form an intermediate stream of cracked gas precooled to a first temperature;

an intermediate cooling and partial condensation stage for the intermediate stream of cracked gas, the intermediate stage comprising an intermediate heat exchanger and an intermediate separating balloon for an intermediate liquid to form a downstream stream of cracked gas cooled to a second temperature below the first temperature;

a downstream cooling and partial condensation stage for the downstream stream of cracked gas to cool the downstream stream of cracked gas to a third temperature below the second temperature, the downstream stage comprising at least one downstream heat exchanger;

a downstream separator and an introducer for introducing the downstream stream of partially condensed cracked gas coming from the downstream heat exchanger into the downstream separator;

a recovery stage, at the head of the downstream separator, for recovering a gaseous stream-of high-pressure fuel, lean in C2+ hydrocarbons, and recovering, at the bottom of the downstream separator, a downstream liquid, rich in C2+ hydrocarbons;

a passage assembly for the stream of high-pressure fuel through the downstream exchanger and the intermediate exchanger to form a stream of reheated high-pressure fuel;

at least first one dynamic expansion device for the stream of reheated high-pressure fuel to obtain a partially expanded fuel stream;

a passage for the stream of partially expanded fuel through the downstream exchanger and the intermediate exchanger to reheat the stream of partially expanded fuel;

a treatment stage for at least one liquid stream obtained in at least one of the upstream cooling, intermediate cooling, and downstream cooling stages to form the ethylene-rich cut;

a former for forming an expanded intermediate recirculation stream from a liquid obtained in at least one of the upstream cooling and/or intermediate cooling stages, upstream from the downstream cooling stage;

a circulator for circulating the expanded intermediate recirculation stream at least in the upstream heat exchanger to cool the upstream stream of cracked gas;

a reintroducer for reintroducing the heated intermediate recirculation stream into the raw cracked gas upstream from at least one compressor of the at least one compressor of the cooling and compression stage, the upstream, intermediate and downstream stages assemblies being configured to respectively cool the upstream stream of cracked gas, the intermediate stream of cracked gas- and the downstream stream of cracked gas without heat exchange with an outside refrigeration cycle, wherein a flow path between the head of the downstream separator and the at least one first dynamic expansion turbine passes through the downstream exchanger and the intermediate exchanger without passing through the upstream heat exchanger.

15. The method according to claim 2, wherein the pressure of the expanded intermediate recirculation stream is comprised between 20% and 50% of the pressure of the compressed cracked gas stream.

16. The method according to claim 3, wherein the pressure of the expanded intermediate recirculation flow is comprised between 5 bars and 20 bars.

17. The method according to claim 4, wherein said molar flow rate is comprised between 30% and 60% of the molar flow rate of the stream of raw cracked gas.

18. The method according to claim 5, wherein said molar ethylene content is comprised between 55% and 65%.

19. The method according to claim 1, wherein the first temperature of the intermediate stream of cracked gas is between −63° C. and −78° C.

20. The method according to claim 1, wherein the compressing of the stream of raw cracked gas is done in at least a first compressor and a second compressor of the at least one compressor of the cooling and compression stage to form the compressed cracked gas stream, the reintroducing of the reheated intermediate recirculation stream in the raw cracked gas being done upstream from the second compressor and downstream from the first compressor.

21. A method for fractionating a stream of cracked gas from a hydrocarbon pyrolysis plant to obtain an ethylene-rich cut and a $C_2^+$ hydrocarbon-lean fuel stream, the method comprising:

compressing the stream of raw cracked gas in at least one compressor of a cooling and compression stage to form a compressed cracked gas stream;

upstream cooling and partial condensing, in at least one upstream heat exchanger, of an upstream stream of cracked gas, obtained from the compressed cracked gas stream, and separation of an upstream liquid in at least one upstream balloon to form an intermediate stream of cracked gas pre-cooled at a first temperature;

intermediate cooling and partial condensation of the intermediate stream of cracked gas in an intermediate heat exchanger and separation of an intermediate liquid in an intermediate separating balloon to form a downstream stream of cracked gas cooled to a second temperature lower than the first temperature;

downstream cooling and partial condensation of the downstream stream of cracked gas in at least one downstream heat exchanger to a third temperature lower than the second temperature;

introducing the downstream stream of partially condensed cracked gas from the downstream heat exchanger in a downstream separator;

recovering, at the head of the downstream separator a gas stream of high-pressure fuel, lean in $C_2^+$ hydrocarbons, and recovering, at the bottom of the downstream separator, a downstream liquid, rich in $C_2^+$ hydrocarbons;

passing of the stream of high-pressure fuel through the downstream exchanger and the intermediate exchanger to form a heated high-pressure fuel stream;

expanding the heated high-pressure fuel stream in at least one first dynamic expansion device to obtain a stream of partially expanded fuel;

heating of the stream of partially expanded fuel through the downstream exchanger and the intermediate exchanger;

treating at least one liquid stream obtained during the upstream cooling, intermediate cooling and downstream cooling to form the ethylene-rich cut;

forming an expanded intermediate recirculation stream from a liquid obtained during the upstream cooling and/or intermediate cooling, upstream from the downstream cooling;

circulating the expanded intermediate recirculation stream at least in the upstream heat exchanger to cool the upstream stream of cracked gas;

reintroducing the reheated intermediate recirculation stream in the raw cracked gas upstream from at least one compressor of the at least one compressor of the cooling and compression stage, the upstream, intermediate and downstream cooling being carried out without heat exchange respectively of the upstream stream of cracked gas, the intermediate stream of cracked gas and the downstream stream of cracked gas with an external refrigeration cycle; and forming an expanded recirculation stream from at least one fraction of the intermediate liquid and/or at least one fraction of the downstream liquid, and introducing the expanded recirculation stream into the downstream heat exchanger, and/or into the intermediate heat exchanger, before mixing the expanded recirculation stream with the raw cracked gas stream before the passage of the raw cracked gas stream in at least one compressor of the at least one compressor of the cooling and compression stage, the pressure of the expanded recirculation stream being lower than the pressure of the expanded intermediate recirculation stream.

* * * * *